United States Patent [19]

Kleiner

[11] Patent Number: 4,751,028
[45] Date of Patent: Jun. 14, 1988

[54] PROCESS FOR THE PREPARATION OF THIOPHOSPHINIC CHLORIDES

[75] Inventor: Hans-Jerg Kleiner, Kronberg, Fed. Rep. of Germany

[73] Assignee: Hoechst Aktiengesellschaft, Frankfurt am Main, Fed. Rep. of Germany

[21] Appl. No.: 82,112

[22] Filed: Aug. 6, 1987

[30] Foreign Application Priority Data

Aug. 9, 1986 [DE] Fed. Rep. of Germany ....... 3627009

[51] Int. Cl.$^4$ ................................................ C07F 9/42
[52] U.S. Cl. ................................. 260/543 P; 558/386
[58] Field of Search ..................... 260/543 P; 558/386

[56] References Cited

U.S. PATENT DOCUMENTS

| | | | |
|---|---|---|---|
| 2,662,917 | 12/1953 | Jensen | 260/543 P |
| 2,882,304 | 4/1959 | Weber | 260/543 P |
| 2,882,315 | 4/1959 | Passino | 260/543 P |
| 2,882,316 | 4/1959 | Hanford | 260/543 P |
| 2,929,843 | 3/1960 | Dawson et al. | 260/543 P |
| 3,008,987 | 11/1961 | Fanhoe | 260/543 P |
| 3,089,890 | 5/1963 | Chupp | 260/543 P |
| 3,360,556 | 12/1967 | Moedritzer | 260/543 P |
| 3,457,306 | 7/1969 | Baker | 260/543 P |
| 3,504,025 | 3/1970 | Maier | 260/543 P |
| 3,689,548 | 9/1972 | Maier | 260/543 P |
| 4,481,151 | 11/1984 | Kleiner | 260/543 P |

FOREIGN PATENT DOCUMENTS

| | | | |
|---|---|---|---|
| 7214241 | 5/1973 | Netherlands | 260/543 P |
| 1162899 | 8/1969 | United Kingdom | 260/543 P |
| 1184767 | 3/1970 | United Kingdom | 260/543 P |

OTHER PUBLICATIONS

V. V. Belakhov et al, Zh. Obshch. Khim. 52, 196–197 (1982) (English Language Edition; original Russian article appears at 52, 214–215.)

Primary Examiner—Paul J. Killos

[57] ABSTRACT

A process for the production of a chloride of thiophosphinic acids which comprises reacting an anhydride of a phosphinic acid with thiophosphoryl chloride.

14 Claims, No Drawings

PROCESS FOR THE PREPARATION OF THIOPHOSPHINIC CHLORIDES

DESCRIPTION

Thiophosphinic chlorides are compounds of the general formula

where R denotes organic radicals. They are mainly intermediates, for example for the preparation of plant-protection agents and peptides.

Various processes are known for the preparation of thiophosphinic chlorides; one such process is, for example, the reaction of phosphinic acids with thiophosphoryl chloride $PSCl_3$ (Zh. Obshch. Khim. Vol. 52, No. 1, pp. 214–215, English edition pp. 195–196 (1982)). The following equation is given for the reaction:

$$R_2P(O)OH + PSCl_3 \rightarrow R_2P(S)Cl$$

According to the 1st illustrative embodiment (Ia), 0.011 mole of the phosphinic acid where $R=C_6H_5CH=CH-$ (=distyrylphosphinic acid) were refluxed for 14 hours with 0.15 mole—i.e. a considerable excess—of $PSCl_3$. The yield of the resulting distyrylthiophosphinic chloride is said to have been 54%.

The further illustrative embodiments were carried out analogously according to the synthesis in the literature citation, with the following yields:

Example Ib

Phosphinic acid where $R=C_6H_5CCl=CH-$ (=di-$\beta$-chlorostyrylphosphinic acid)→di-$\beta$-chlorostyrylthiophosphinic chloride—yield 53%

Example Ic

Phosphinic acid where $R=C_2H_5-$ (=diethylphosphinic acid)→diethylthiophosphinic chloride—yield 52%; and

Example Id

Phosphinic acid where $R=C_6H_5-$ (=diphenylphosphinic acid)→diphenylthiophosphinic chloride—yield 33%.

The starting phosphinic acids can be obtained by various processes. For example, diethylphosphinic acid can be obtained from the appropriate phosphinic anhydride and hydrogen halide by the process according to German Offenlegungsschrift No. 3,135,666. For the method described in Zh. Obshch. Khim. (in loco citato), the large excesses of thiophosphoryl chloride, the long reaction duration and the only moderate yields are disadvantageous.

A further method of preparing thiophosphinic chlorides is the reaction of phosphinic chloride with thiophosphoryl chloride at temperatures of 140°–250° C. and approximately atmospheric pressure with continuous distillation of the phosphorus oxychloride formed (German Offenlegungsschrift No. 2,623,845). The following equation can be given for this reaction:

$$R_2P(O)Cl + PSCl_3 \rightarrow R_2P(S)Cl + POCl_3$$

The phosphinic chloride employed here as starting material can be obtained from the appropriate phosphinic acid esters and inorganic acid halides of the formula $(YO)_n X_2$, in which Y denotes C or S, X denotes halogen, and n denotes the number 1 or 2 when Y=C and denotes the number 1 when Y=S, via the phosphinic anhydride (German Offenlegungsschrift No. 2,129,583); for example, using $COCl_2$ as the inorganic acid halide, the reaction may be represented by the following equations:

$$2R_2P(O)OR' + COCl_2 \rightarrow R_2P(O)-O-(O)PR_2 + CO_2 + 2R'Cl$$

$$R_2P(O)-O-(O)PR_2 + COCl_2 \rightarrow 2R_2P(O)Cl + CO_2$$

(R and R'=organic radicals).

In order to obtain thiophosphinic chlorides by the last described route, it is thus necessary—when starting from phosphinic acid esters—to carry out several process steps.

In attempting to provide an improved process for the preparation of thiophosphinic chlorides, it has now been found that this object can be achieved by reacting phosphinic anhydrides with thiophosphoryl chloride in a single process step.

Accordingly, the invention relates to a process for the preparation of thiophosphinic chlorides by reacting phosphinic acid derivatives with thiophosphoryl chlorides; the process comprises using phosphinic anhydrides as phosphinic acid derivatives. The reaction may be described by the following equation:

$$3R_2P(O)-O-(O)PR_2 + 6PSCl_3 \rightarrow 6R_2P(S)Cl + 4POCl_3 + P_2O_5$$

(R=organic radicals).

In this process—starting from phosphinic anhydrides—products of high purity are obtained in good yields (at least 80%) in a single process step in relatively short reaction times without using excess amounts of the starting material. This is extremely surprising since only moderate yields (at most 53%) are achieved in the reaction of phosphinic acid with thiophosphoryl chloride (Zh. Obshch. Khim., in loco citato) using a large excess of thiophosphoryl chloride and relatively long reaction times.

In principle, the starting compounds used for the process according to the invention can be all possible phosphinic anhydrides. Those phosphinic anhydrides of the general formula given above in which the radicals R denote identical or different alkyl and/or alkenyl radicals, i.e. those having only one olefinic bond—which may all be further substituted by one or more inert groups—or mononuclear aromatic hydrocarbon radicals are preferably employed. Inert substituents of the alkyl and/or alkenyl radicals are substituents which do not react under the reaction conditions, i.e., for example, halogen or alkoxy, cyano or phenyl groups; preferred substituents are chlorine and alkoxy groups, alkoxy groups containing 1–4 carbon atoms being particularly preferred. Possible mononuclear aromatic hydrocarbons are, above all, unsubstituted phenyl radicals, but also, in addition, those which are substituted by a maximum of two straight-chain or branched alkyl groups having 1–4 carbon atoms, but which contain a total of no more than 10 carbon atoms. Apart from phenyl radicals, alkyl radicals having a total of 1-20 carbon atoms and alkenyl radicals having a total of 2-20 carbon atoms are preferred; alkyl radicals having a total of 1-5 carbon atoms are particularly preferred.

Examples of starting compounds—preferred and otherwise—are thus:

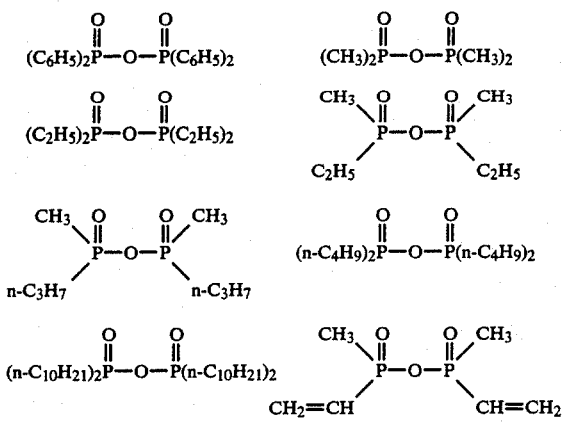

etc.

The starting phosphinic anhydrides are prepared by conventional processes, such as described above, for example, in connection with German Offenlegungsschrift No. 2,129,583.

The second starting material $PSCl_3$ is a conventional commercial product; if necessary, it may also be generated in situ from $PCl_3$ and sulfur.

According to the reaction equation, phosphinic anhydrides and thiophosphoryl chloride are employed in the ratio 1:2; the use of the starting materials in this molar ratio (exactly or at least approximately) is also preferred. The reaction can also be carried out using an excess of thiophosphoryl chloride, but this offers no advantage.

In principle, the reaction can proceed in a broad temperature range; it is preferably carried out at temperatures between about 80° and 250° C., in particular between about 100° and 200° C., and, when aliphatic phosphinic anhydrides are used, between about 100° and 170° C. The process is otherwise conducted in a fashion which is conventional per se. One starting component—either phosphinic anhydride or thiophosphoryl chloride—is normally heated to the reaction temperature (preferably with stirring), and the other component—i.e. thiophosphoryl chloride or phosphinic anhydride respectively—is subsequently added dropwise—preferably within about 2 to 5 hours. The phosphorus oxychloride formed in the reaction is expediently removed by distillation—preferably via a column. The reaction product produced is preferably purified by distillation—if appropriate under reduced pressure. The invention is now illustrated in greater detail by the examples below.

EXAMPLES

1. Methylethylthiophosphinic chloride.

511 g (3.02 mol) of thiophosphoryl chloride were heated to 110° C. with stirring, and 272 g (1.37 mol) of methylethylphosphinic anhydride were then added dropwise over 2 hours; at the same time, the temperature was increased slowly to 140° C. Phosphorus oxychloride distilled off via an 80 cm silver-jacket packed column. The mixture was subsequently stirred for a further 6 hours and, at the same time, the internal temperature increased to 170° C. After cooling, the reaction mixture produced was subsequently distilled without using a column. 312 g of 96.5% pure methylethylthiophosphinic chloride (b.p. 70° C.; 0.1333 kPa) were obtained. 135 g remained as residue. The yield is 80% of theory, relative to the methylethylphosphinic anhydride employed.

2. Methyl(n-propyl)thiophosphinic chloride.

56.6 g (0.25 mol) of methyl(n-propyl)phosphinic anhydride were gradually heated over 5 hours to a final temperature of 150° C. with stirring and continuous addition of thiophosphoryl chloride, in total 84.5 g (0.5 mol). Phosphorus oxychloride distilled off. After cooling, the residue was distilled at 0.067 kPa at a transition temperature of 70° C. to an internal temperature of 135° C. 65 g of methyl(n-propyl)thiophosphinic chloride were obtained. This corresponds to a yield of 83% of theory.

3. Diphenylthiophosphinic chloride.

209 g (0.5 mol) of diphenylphosphinic anhydride were heated to 180°–190° C. and then added dropwise over several hours with stirring to an excess of thiophosphoryl chloride; during this, phosphorus oxychloride distilled off through a column together with unreacted thiophosphoryl chloride. When the reaction was complete, the reaction mixture was distilled under reduced pressure through a thin-film evaporator. Distillation was subsequently effected without using a column. 200 g of diphenylthiophosphinic chloride (b.p. 170° C.; 0.053 kPa) were obtained. This corresponds to a yield of 79% of theory.

I claim:

1. A process for the production of a chloride of thiophosphinic acids which comprises reacting an anhydride of a phosphinic acid with thiophosphoryl chloride.

2. A process as claimed in claim 1, wherein the anhydride of phosphinic acid has the formula

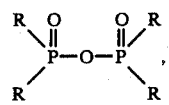

wherein the groups R are equal or different and represent at least one member of the group consisting of alkyl and alkenyl, each of which is unsubstituted or substituted by a group which is inert under the reaction conditions towards the reactants.

3. A process as claimed in claim 2, wherein the inert group is halogen, alkoxy, cyano, phenyl or combinations thereof.

4. A process as claimed in claim 3, wherein the inert group is chlorine or alkoxy having from 1 to 4 carbon atoms.

5. A process as claimed in claim 2, wherein the alkyl and alkenyl groups each have a total of 1 to 20 carbon atoms.

6. A process as claimed in claim 5, wherein the alkyl groups each have a total 1 to 5 carbon atoms.

7. A process as claimed in claim 1, wherein the anhydride of the phosphinic acid and the thiophosphoryl chloride are applied in a molar ratio of about 1:2.

8. A process as claimed in claim 1, wherein the reaction is carried out at a temperature in the range of from about 80° to 250° C.

9. A process as claimed in claim 8, wherein the reaction is carried out at a temerature in the range of from 100° to 200° C.

10. A process as claimed in claim 9, wherein the reaction is carried out at a temperature in the range of from 100° to 170° C.

11. A process as claimed in claim 1, wherein phosphorus oxychloride formed during the reaction is continuously distilled off.

12. A process as claimed in claim 1, wherein the anhydride of the phosphinic acid has the formula shown in claim 2 with the modification that at least one group R is a mononuclear aromatic hydrocarbon group which contains up to 10 carbon atoms and is unsubstituted or substituted by at most 2 alkyl groups.

13. A process as claimed in claim 12, wherein all groups R are phenyl.

14. A process or the production of a chloride of thiophosphinic acids which comprises reacting an anhydride of a phosphinic acid with thiophosphoryl chloride in a molar ratio of about 1:2 at a temperature in the range of from about 100° to 170° C. while continuously distilling off phosphorus oxychloride which is formed during the reaction, the anhydride of the phosphinic acid having the formula

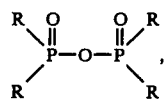

in which the groups R are equal or different alkyl groups having from 1 to 5 carbon atoms.

* * * * *